(12) United States Patent
Roshdy

(10) Patent No.: US 6,691,868 B2
(45) Date of Patent: Feb. 17, 2004

(54) KIT PACKAGE FOR MULTIPLE SMALL DEVICES

(75) Inventor: Constance E. Roshdy, Mount Bethel, PA (US)

(73) Assignee: Ethicon, Inc., Somerville, NJ (US)

(*) Notice: Subject to any disclaimer, the term of this patent is extended or adjusted under 35 U.S.C. 154(b) by 86 days.

(21) Appl. No.: 10/039,192

(22) Filed: Dec. 31, 2001

(65) Prior Publication Data
US 2003/0121811 A1 Jul. 3, 2003

(51) Int. Cl.[7] ............................................. B65D 83/10
(52) U.S. Cl. ......................... 206/366; 206/485; 206/486
(58) Field of Search .......................... 206/363, 364–370, 206/438, 439, 485, 486, 476, 372, 373

(56) References Cited

U.S. PATENT DOCUMENTS

| | | | |
|---|---|---|---|
| 1,367,600 A | * 2/1921 | Hirsch | ...................... 206/485 |
| 1,446,741 A | 2/1923 | Faber | |
| 2,025,522 A | 12/1935 | Myers | |
| 2,224,027 A | 12/1940 | Tate | |
| 2,944,665 A | 7/1960 | Obeck | |
| 2,974,782 A | * 3/1961 | Walters | ...................... 206/485 |
| 3,058,584 A | 10/1962 | Marshall | |
| 3,153,531 A | 10/1964 | Cook | |
| 3,248,017 A | 4/1966 | Allen | |
| 3,497,982 A | 3/1970 | Schulz | |
| 3,698,551 A | 10/1972 | Tomlinson | |
| 3,927,762 A | 12/1975 | Zdarsky et al. | |
| 3,951,261 A | 4/1976 | Mandel et al. | |
| 3,951,263 A | 4/1976 | Vale | |
| 4,023,678 A | 5/1977 | Fiedler | |
| 4,091,927 A | 5/1978 | Lunsford | |
| 4,424,898 A | 1/1984 | Thyen et al. | |
| 4,619,364 A | 10/1986 | Czopor, Jr. | |
| 4,915,233 A | 4/1990 | Smith | |
| 5,024,323 A | 6/1991 | Bolton | |
| 5,099,994 A | 3/1992 | Kalinski et al. | |
| 5,322,163 A | 6/1994 | Foos | |
| 5,323,907 A | 6/1994 | Kalvelage | |
| 5,351,822 A | 10/1994 | Sinn | |
| 5,353,922 A | 10/1994 | Sinn | |
| 5,358,116 A | * 10/1994 | Brintazzoli | ................. 206/485 |
| 5,361,907 A | * 11/1994 | Mohrhauser | ................ 206/528 |
| 5,375,717 A | * 12/1994 | Roshdy | ..................... 206/476 |
| 5,392,919 A | * 2/1995 | Passamoni | ................. 206/576 |
| 5,477,964 A | 12/1995 | Hart | |
| 5,544,755 A | * 8/1996 | Paumen et al. | ............. 206/705 |
| 5,575,382 A | 11/1996 | Sobel et al. | |
| 5,577,606 A | * 11/1996 | Schwentuchowski et al. | .... 206/327 |
| 5,617,952 A | 4/1997 | Kranendonk | |
| 5,699,909 A | 12/1997 | Foster | |
| 5,704,469 A | 1/1998 | Daniele et al. | |
| 5,788,062 A | 8/1998 | Cerwin et al. | |
| 5,788,063 A | 8/1998 | Van Ness | |
| 5,928,611 A | 7/1999 | Leung | |
| 6,394,269 B1 | * 5/2002 | Rudnick et al. | ............ 206/380 |

* cited by examiner

Primary Examiner—Shian Luong

(57) ABSTRACT

A retainer card is disclosed which includes a pair of fold lines, a main section, and a center section. Opening(s) formed in the main section cooperate with opening(s) formed in the center section so as to form at least one receptacle for a surgical or medical device. The main section is deflectable from a relaxed configuration to a flexed configuration when a surgical or medical device is inserted into a corresponding one of the receptacle(s). The retainer card and the surgical or medical device(s) contained therein can be inserted into an outer sterilizable envelope.

24 Claims, 6 Drawing Sheets

KIT PACKAGE FOR MULTIPLE SMALL DEVICES

FIELD OF THE INVENTION

The present invention relates to a kit package, and more specifically to a package assembly that holds and displays multiple surgical devices therein.

BACKGROUND OF THE INVENTION

Typically, medical or surgical devices are packaged in convenient kits. There remains a need for a kit that organizes the surgical devices for ease of access. The kit should also fit into existing secondary and tertiary packaging.

DESCRIPTION OF THE RELATED ART

U.S. Pat. No. 5,699,909 to Foster discloses a foldable plastic retainer having a display area for locking multiple endoscopic instruments in place.

U.S. Pat. No. 2,224,027 to Tate discloses a door key display card having securing means for holding a door key thereon.

U.S. Pat. No. 2,025,522 to Meyers discloses a display device having holding sections being in a triangular folded configuration for holding a plurality of cylindrical articles.

U.S. Pat. No. 1,446,741 to Farber discloses a display card for holding pencils that includes fold sections having openings for receiving pencils therein.

SUMMARY OF THE INVENTION

In accordance with the present invention, a retainer card is made of a planar sheet and includes a first foldable panel having a first fold line and a second fold line positioned on one side of the first fold line, a main section positioned on an opposite side of the first fold line, and a center section positioned between the first and second fold lines. At least one opening is formed in the main section, while at least another opening is formed in the center section. The opening(s) in the main section cooperate with the opening(s) in the center section to form at least one receptacle for a surgical or medical device when the main and center sections are folded relative to one another about the first fold line. The main section is deflectable from a relaxed configuration to a flexed configuration in response to the insertion of a surgical or medical device into the receptacle(s), thereby securely attaching one or more such devices to the retainer card. The retainer card and its associated medical or surgical devices are adapted for insertion into an outer sterilizable envelope, whereby the surgical or medical devices can be stored in a sterile environment.

BRIEF DESCRIPTION OF THE DRAWINGS

Further objects, features and advantages of the present invention will become apparent upon consideration of the following detailed description of the exemplary embodiments considered in connection with the accompanying drawings, in which.

DETAILED DESCRIPTION OF THE PREFERRED EMBODIMENTS

Figure 1:
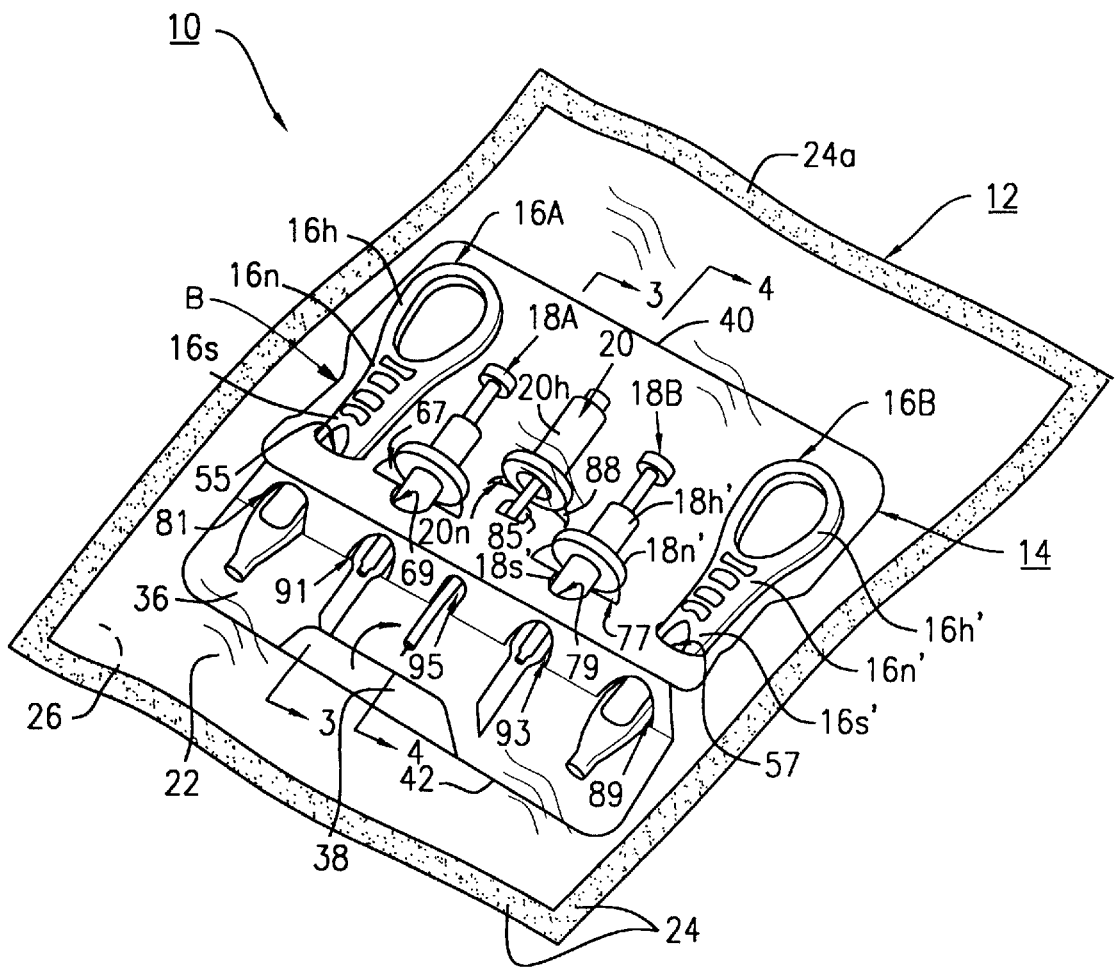
FIG. 1 is a front perspective view of a kit package assembly constructed in accordance with a first exemplary embodiment of the present invention.

Referring to FIGS. 1 through 5, there is shown a kit package assembly 10 constructed in accordance with a first embodiment of the present invention. The kit package assembly 10 includes an outer containment envelope or pouch 12 and a retainer card 14 for holding one or more surgical instruments 16A, 16B, 18A, 18B and 20 in place. In particular, the surgical instruments include two inserters 16A, 16B, two inverters 18A, 18B and a single surgical snare device or instrument 20, as depicted in FIG. 1. As shown in FIGS. 1 through 4, the first inserter surgical instrument 16A includes a handle member 16$h$, a flange member 16$n$ and an elongated shaft 16$s$ extending from its respective flange member 16$n$. The second inserter surgical instrument 16B includes a handle member 16$h$', a flange member 16$n$' and an elongated shaft 16$s$' extending from its respective flange member 16$n$'. The first inverter surgical instrument 18A includes a handle member 18$h$, a flange member 18$n$ and an extended shaft section 18$s$ extending from its respective flange member 18$n$. The second inverter surgical instrument includes a handle member 18$h$', a flange member 18$n$' and an extended shaft section 18$s$' extending from its respective flange member 18$n$'. The surgical snare device 20 includes a handle member 20$h$, a flange member 20$n$, an elongated shaft section 20$s$ extending from its respective flange member 20$n$, and a sharp end tip 20$t$.

Figure 2:
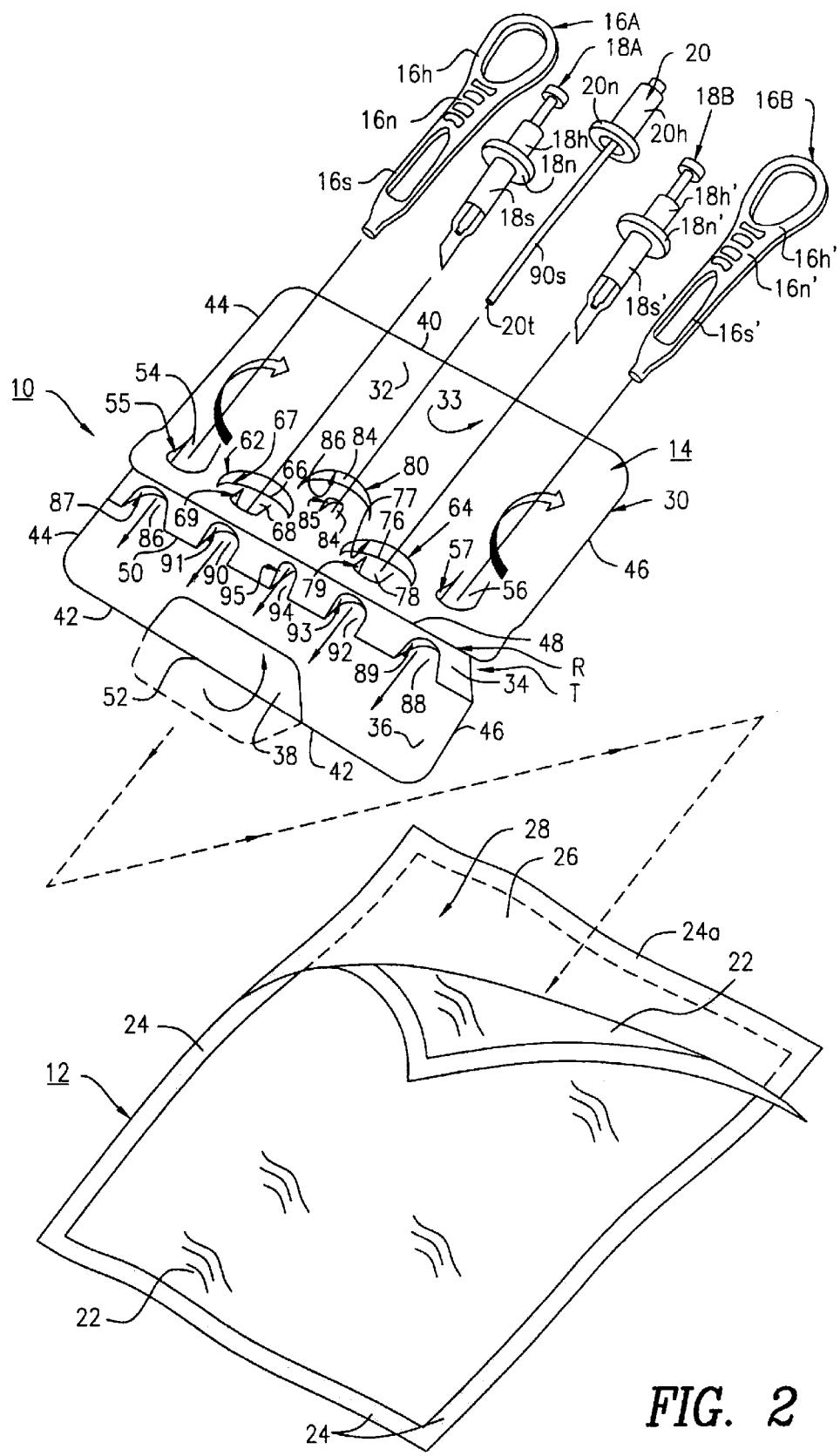
FIG. 2 is an exploded perspective view of the kit package assembly of FIG. 1.

Referring to FIG. 2, the outer containment envelope 12 includes a front cover sheet 22 made of clear plastic material having a bonded perimeter edging 24 connected to a rear paper sheet 26 for forming an interior compartment 28 sized and shaped to hold the retainer card 14 therein. The bonding is achieved by any of the methods conventionally used in the art, such as heat sealing, adhesives, and the like. The interior compartment 28 and the surgical instruments within the outer containment envelope 12 can be sterilized by conventional means such as ethylene oxide, gamma irradiations and the like.

Figure 3:
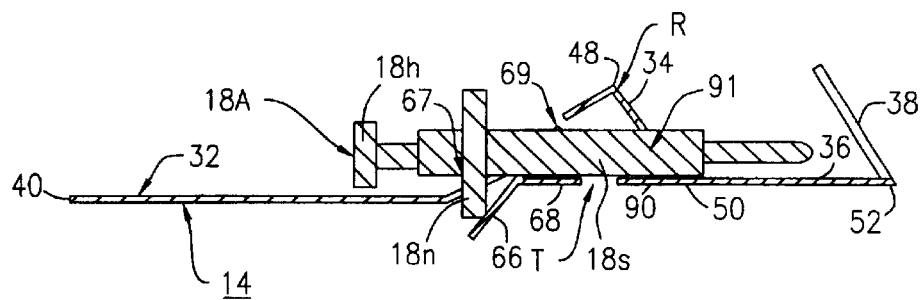
FIG. 3 is a cross-sectional view, taken along section line 3—3 and looking in the direction of the arrows, of a retainer card of FIG. 1.
Figure 4:
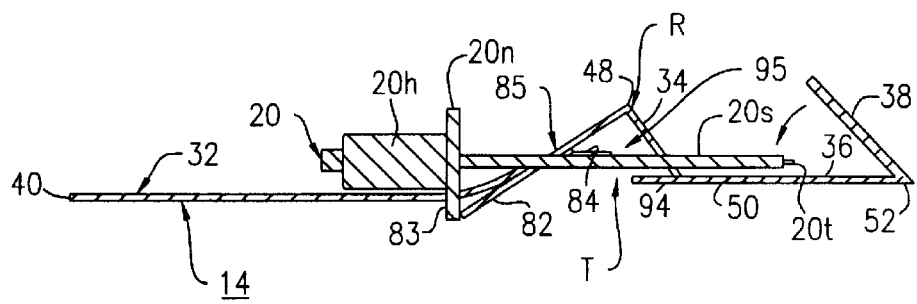
FIG. 4 is a cross-sectional view taken along section line 4—4 and looking in the direction of the arrows, of the retainer card of FIG. 1.
Figure 5:
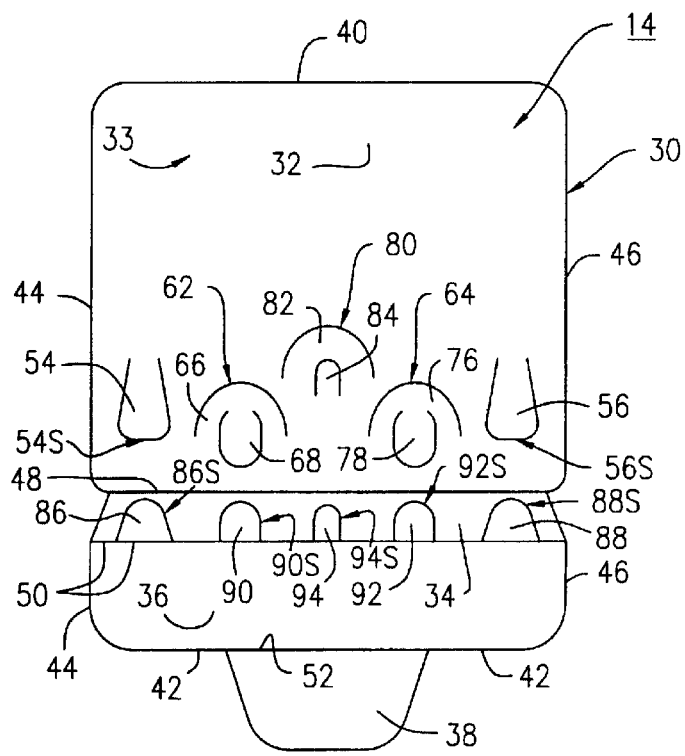
FIG. 5 is a front elevational view of the retainer card of FIG. 1 showing a blank paperboard configuration.

In reference to FIGS. 2 and 5, the retainer card 14 is formed from a thin cardboard blank 30. The retainer card 14 is typically made from paper that has sufficient stiffness to hold the surgical instruments 16A, 16B, 18A, 18B and 20 in place within the containment envelope 12. Alternatively, the retainer card 14 can be constructed from materials of any relative stiffness including paperboard, cardboard or flexible plastic, etc. The retainer card 14 is substantially rectangular-shaped and includes an upper panel section 32, a center fold (panel) section 34, a lower panel section 36 and a bottom U-shaped flap 38. The retainer card 14 further includes a front wall surface 33 for inclusion of graphics, indicia and the like. The retainer card 14 also includes an upper (distal) edge 40, a lower (proximal) edge 42 and side edges 44 and 46. The retainer card 14 further includes a first fold line 48, a second fold line 50 and a third fold line 52. The first and second fold lines 48 and 50 define the area included in the center fold section 34. The first fold line 48 separates the upper panel section 32 from the center fold section 34, and the second fold line 50 separates the center fold section 34 from the lower panel section 36. The third fold line 52 separates the lower panel section 36 from the bottom U-shaped flap 38. The upper section 32 of retainer card 14 supports the handle members 16h, 16h', 18h, 18h' and 20h and the flange members 16n, 16n', 18n, 18n' and 20n of surgical instruments 16A, 16B, 18A, 18B and 20, respectively, as depicted in FIG. 1. The center fold section 34 of retainer card 14 supports and holds in place the elongated shafts 16s, 16s', 18s, 18s' and 20s of surgical instruments 16A, 16B, 18A, 18B and 20 as depicted in FIGS. 1 and 3. The lower section 36 also supports the lower portion of the elongated shafts 16s, 16s', 18s, 18s' and 20s of surgical instruments 16A, 16B, 18A, 18B and 20 as shown in FIG. 1. The bottom U-shaped flap 38 is bent upwardly about fold line 52 to cover the sharp end tip 20t of the snare device 20, as shown in FIGS. 1, 2 and 4.

Again referring to FIGS. 2 and 5, the upper panel section 32 includes a pair of elongated and vertically extending U-shaped cuts 54S, 56S. The first U-shaped cut 54S forms a tab 54 being adjacent to side edge 44 and the U-shaped cut 54S also forms a first vertically extending opening 55 when the tab 54 is pushed inwardly. The second U-shaped cut 56S forms a tab 56 being adjacent to side edge 46 and the U-shaped cut 56S also forms a second vertically extending opening 57 when the tab 56 is pushed inwardly. The upper panel section 32 further includes a pair of inverted U-shaped cuts 62, 64. The first inverted U-shaped cut 62 forms a first upper inverted U-shaped tab 66 and also forms a first lower oval-shaped tab 68. The first inverted U-shaped cut 62 forms a first upper inverted U-shaped opening 67 when the tab 66 is pushed inwardly, and similarly the first U-shaped cut 62 also forms a first lower oval-shaped opening 69 when the tab 68 is pushed inwardly. The first inverted U-shaped cut 62 is adjacent to the first vertically extending U-shaped cut 54S as depicted in FIG. 5. Similarly, the second inverted U-shaped cut 64 forms a second upper inverted U-shaped tab 76 and also forms a second lower oval-shaped tab 78. The second inverted U-shaped cut 64 forms a second upper inverted U-shaped opening 77 when the tab 76 is pushed inwardly, and similarly, the second inverted U-shaped cut 64 also forms a second lower oval-shaped opening 79 when the tab 78 is pushed inwardly. The second inverted U-shaped cut 64 is adjacent to the second vertically extending U-shaped cut 56S as depicted in FIG. 5. The upper panel section 32 also includes a center inverted U-shaped cut 80. The center inverted U-shaped cut 80 forms an upper center inverted U-shaped tab 82 and also forms a lower center oval-shaped tab 84. The center inverted U-shaped cut 80 forms an upper center inverted U-shaped opening 83 when the tab 82 is pushed inwardly, and similarly, the center inverted U-shaped cut 80 also forms a lower center oval-shaped opening 85 when the tab 84 is pushed inwardly. The center inverted U-shaped cut 80 is adjacent and centrally positioned to each of the inverted U-shaped cuts 62, 64 as shown in FIGS. 2 and 5.

Still referring again to FIGS. 2 and 5, the center fold section 34 includes a pair of conically-shaped cuts 86S and 88S. The first conically-shaped cut 86S forms a tab 86 being adjacent to side edge 44 and cut 86S also forms conically-shaped opening 87 when the tab 86 is pushed inwardly. The second conically-shaped cut 88S forms a tab 88 being adjacent to side edge 46 and cut 88S also forms a conically-shaped opening 89 when the tab 88 is pushed inwardly. The center fold section 34 further includes a pair of inverted U-shaped cuts 90S, 92S. The first inverted U-shaped cut 90S forms a tab 90 being adjacent to the first conically-shaped cut 86S and cut 90S also forms a first inverted U-shaped opening 91 when the tab 90 is pushed inwardly. The second inverted U-shaped cut 92S forms a tab 92 being adjacent to the second conically-shaped cut 88S and cut 92S also forms a second inverted U-shaped opening 93 when the tab 92 is pushed inwardly. The center fold section 34 also includes a center inverted U-shaped cut 94S. The center inverted U-shaped cut 94S forms a center inverted U-shaped opening 95 when the tab 94 is pushed inwardly. The center inverted U-shaped opening 95 is slightly smaller than the inverted U-shaped openings 91 and 93. The center inverted U-shaped cut 94S is adjacent and positioned centrally to each of the inverted U-shaped cuts 90S, 92S as shown in FIG. 5.

In operation, the retainer card 14 is initially bent about fold lines 48 and 50 in preparation for the insertion of the multiple surgical instruments 16A, 16B, 18A, 18B and 20 by a packer. It should be understood that the retainer card 14 includes a relaxed configuration A (see FIG. 2—no surgical instruments are attached to the retainer card 14) being transformable from the relaxed configuration A to a flexed configuration B (see FIG. 1), wherein the retainer card 14 is biased towards the relaxed configuration A. Further, the upper panel section 32 and the center fold section 34 are deflectable into the flexed configuration B (see FIGS. 3 & 4) in response to the insertion of one or more of the surgical instruments (i.e., surgical instruments 18A, 18B or 20 within the retainer card 14), wherein, for example, at least one of the openings 85 of the upper panel section 32 is aligned with at least one of the other openings 95 of the center fold section 34 in order to receive and hold in place the snare device 20 therein, as shown in FIG. 4. The aforementioned packing process has the retainer card 14 bearing upon the surgical instrument (see FIGS. 3 and 4) as the upper panel section 32 of retainer card 14 is moveable towards its relaxed configuration A from its flexed configuration B (but not truly ever getting back to its relaxed configuration A). It should be noted, when the retainer card 14 is in its fully relaxed configuration A, the openings 55, 57, 69, 79 and 85 of the upper panel section are not structurally aligned with the openings 87, 89, 91, 93 and 95 of the center fold section 34 until the upper panel section 32 and the center fold section 34 are deflected to the flexed configuration B with the insertion, for example, of a surgical instrument 20 through aligned openings 85 and 95, as depicted in FIG. 4. Further, the upper panel section 32 and the center fold section 34 are deflectable from the relaxed, planar configuration to the flexed configuration in which the first fold line 48 forms a ridge R (see FIGS. 2–4) and in which the center fold section 34 assumes an angular position relative to the upper panel section 32 to thereby from a trough T (see FIGS. 2–4) underlying the ridge R. As shown in FIG. 2, the tab 68 of the upper panel section 32 section is attached to an edge of the opening 69. With reference to FIG. 3, the tab 68 extends into the trough T in a first direction, and the tab 90 of the lower panel section 36 extends into the trough T in a second direction which is substantially opposite the first direction.

In the continued preparation of the retainer card 14 for packing of the aforementioned surgical instruments, the packer depresses tabs 54, 56, 66, 68, 76, 78, 82 and 84 inwardly which then exposes openings 55, 57, 67, 69, 77, 79, 83 and 85 on the upper panel section 32 of retainer card 14. The packer now proceeds to inwardly depress tabs 86, 88, 90, 92 and 94 which then exposes openings 87, 89, 91, 93 and 95 on the center fold section 34 of retainer card 14. As shown in FIG. 2, this packing procedure by the packer then structurally aligns the openings within the upper panel section 32 and the center fold section 34 as follows: opening 55 vertically aligns with opening 87 in order to accept the shaft portion 16s' of the first inserter instrument 16A, opening 57 vertically aligns with opening 89 in order to accept the shaft portion 16s' of the second inserter instrument 16B, openings 67 and 69 vertically aligns with opening 91 in order to accept the flange member 18n in opening 67 and the shaft portion 18s' within openings 69 and 91 of the first inverter instrument 18A, openings 77 and 79 vertically align with opening 93 in order to accept the flange member 18n' in opening 77 and the shaft portion 18s' within openings 79 and 93 of the second inverter instrument 18B, and openings 83 and 85 vertically align with opening 95 in order to accept the flange members 20n in opening 83 and the shaft portions 20s within openings 85 and 95 of the (center positioned) surgical snare device 20. Preferably, surgical instruments 18A, 20 and 18B are respectively inserted within the retainer card 14 initially (first) by the packer, and then, surgical instruments 16A and 16B are respectively inserted within the retainer card 15 by the packer. In the inserting of each of surgical instruments 16A and 16B by the packer, the shaft portions 16s are inserted from a side orientation and then twisted flat into its place, as depicted in FIG. 2. This aforementioned action locks and holds the two surgical instruments 16A and 16B in place and also stabilizes the retainer card 14, thus preventing the fold lines 48 and 50 from moving. The above operation now positions and locks all of the instruments 16A, 16B, 18A, 18B and 20 within the confines of retainer card 14. The packer now proceeds to bend upward the U-shaped bottom flap 38 along fold line 52, such that the bottom flap 38 covers the end tip 20t of the snare device 20, as depicted in FIG. 4.

As shown in FIG. 1, the retainer card 14 having the multiple surgical instruments 16A, 16B, 18A, 18B and 20 retained or contained therein, the retainer card 14 is then placed within the interior compartment 28 of the outer containment envelope 12 and the upper perimeter edge 24a of the outer containment envelope 12 is sealed shut, thus forming the kit package assembly 10 of the present invention. The retainer card 14 is positioned within the outer envelope 12 such that the multiple surgical instruments 16A, 16B, 18A, 18B and 20 are facing the clear (see through) front cover sheet 22. The kit package assembly 10 can also be used with existing secondary and tertiary packaging. Additionally, the present invention is related to commonly owned copending application Serial No. 10/039,173, entitled, "Blister Tray With A Package For A Small Device", docket number ETH-1608, and filed contemporaneously herewith. The present invention is also related to commonly owned copending application Serial No. 10/039,172, entitled, "Blister Tray With A Blister Card", docket number ETH-1609,and filed contemporaneously herewith. Both of these related applications are incorporated herein by reference.

Figure 6:
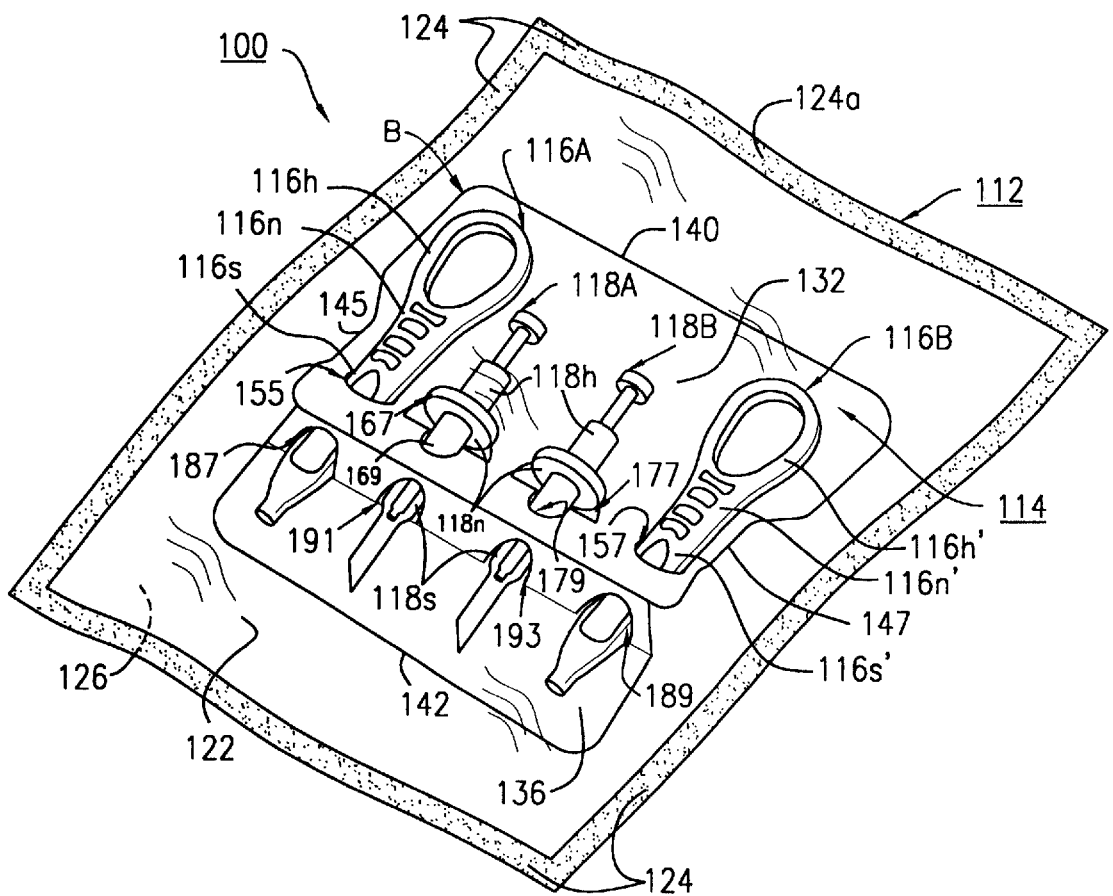
FIG. 6 is a front perspective view of a kit package assembly constructed in accordance with a second exemplary embodiment of the present invention.
Figure 7:
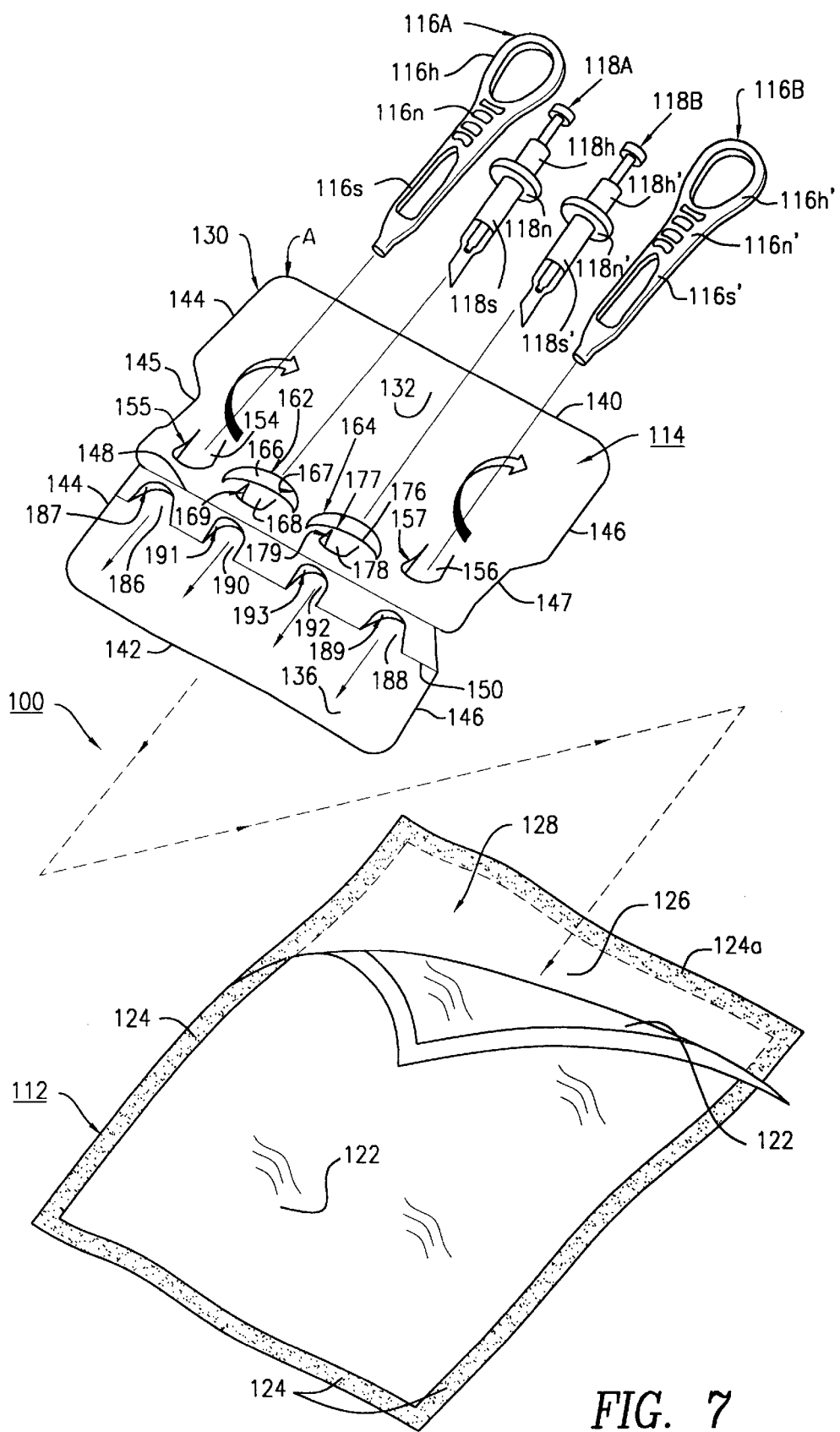
FIG. 7 is an exploded perspective view of the kit package assembly of FIG. 6.
Figure 8:
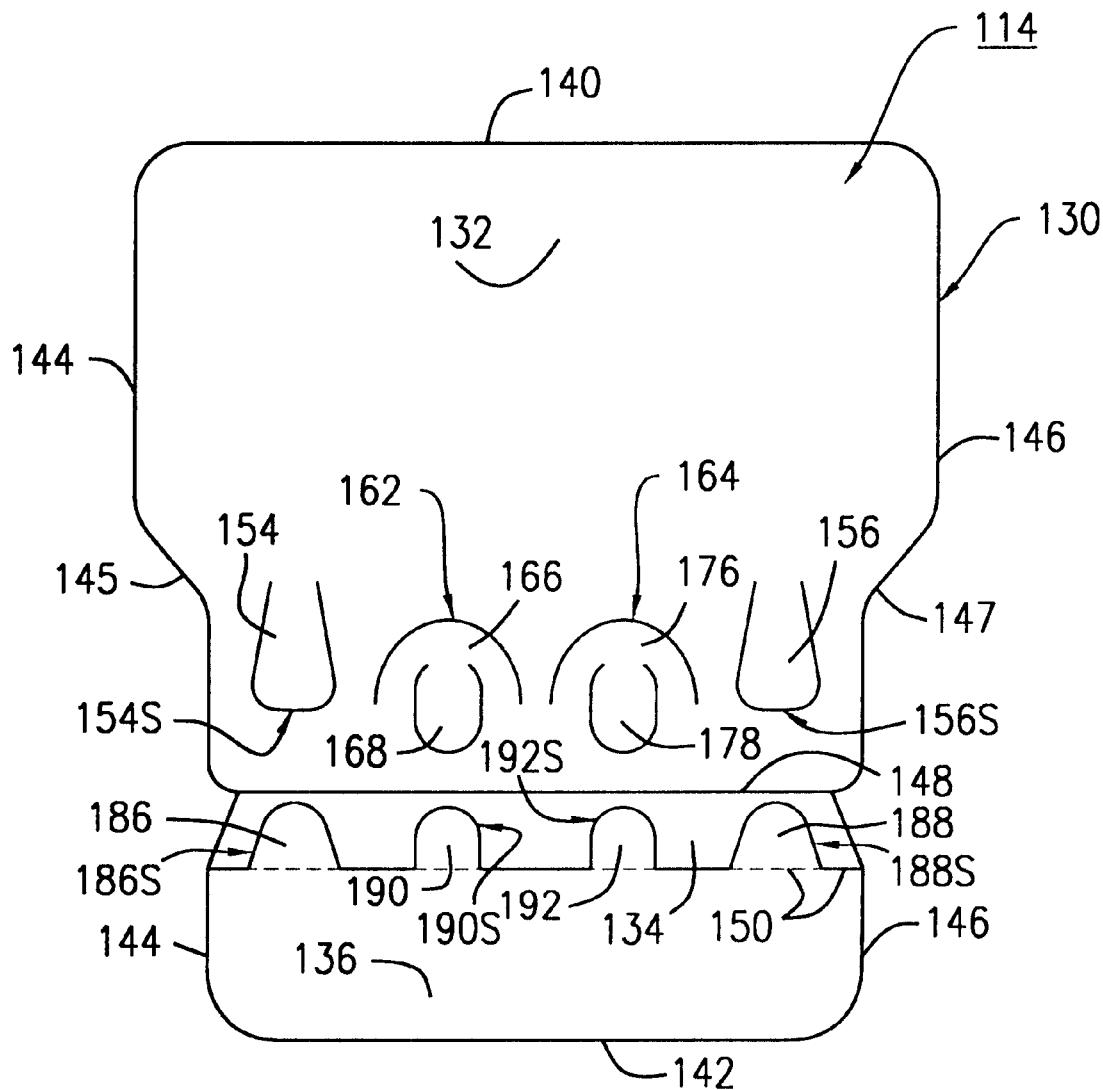
FIG. 8 is a front elevational view of a retainer card of FIG. 6 showing a blank paperboard configuration.

A secondary exemplary embodiment 100 of the present invention is illustrated in FIGS. 6 to 8. Elements illustrated in FIGS. 6 to 8 which correspond to the elements described above with reference to FIGS. 1 through 5 have been designated by corresponding reference numbers increased by one hundred. The second embodiment 100 is constructed and operates in the same manner as the first embodiment 10, unless it is otherwise stated.

With reference to FIGS. 7 and 8, the upper section 132 of retainer card 114 does not include the center inverted U-shaped cut 80 (see FIG. 5) and the center fold section 134 of retainer card 114 does not include the center inverted U-shaped cut 94S (see FIG. 5) which are employed by the first embodiment 10. Further, the bottom section 136 of retainer card 114 does not include a bottom U-shaped flap 38 which is employed by the first embodiment 10. The left side edge 144 includes a recessed and curved edge 145 and the right side edge 146 also includes a recessed and curved edge 147. The recessed and curved edges 145 and 147 are used by the surgeon in order to better grip the retainer card 114 when taking out any of the surgical instruments 116A, 116B, 118A or 118B. All of the above component parts of the second embodiment 100 are exactly the same as those of the first embodiment 10.

It should be understood that the embodiments described herein are merely exemplary and that a person skilled in the art may make many variations and modifications without departing from the spirit and scope of the present invention. For example, the retainer card can be sized and shaped to hold a single surgical or medical device or any other number of such devices. All such variations and modifications are intended to be included within the scope of the invention as defined in the appended claims.

What is claimed is:

1. A retainer card made from a planar sheet, comprising: a foldable panel including a main section, a center section, and an end section, said main section connected to said center section at a first fold line along one side of said center section, said end section connected to said center section at a second fold line along an opposite side of said center section, said center section positioned between said first fold line and said second fold line, said main section and said center section being deflectable from a relaxed, planar configuration to a flexed configuration in which said first fold line forms a ridge and in which said center section assumes an angular position relative to said main section to thereby from a trough underlying said ridge, at least one opening formed in said main section, and at least another opening formed in said center section, said at least another opening cooperating with said at least one opening to form at least one receptacle for a medical device when said main section and said center section are folded into said flexed configuration, said main section including at least one tab attached to an edge of said at least one opening and extending into said trough in a first direction, and said end section including at least another tab extending into said trough in a second direction substantially opposite said first direction.

2. A retainer card in accordance with claim 1, wherein said at least one opening includes a first set of spaced-apart openings.

3. A retainer card in accordance with claim 2, wherein said first set of openings is formed in said main section.

4. A retainer card in accordance with claim 3, wherein said first set of openings is positioned substantially adjacent to said first fold line.

5. A retainer card in accordance with claim 4, wherein said at least another opening includes a second set of spaced-apart openings.

6. A retainer card in accordance with claim 5, wherein said second set of openings is formed in said center section.

7. A retainer card in accordance with claim 6, wherein said second set of openings is positioned substantially adjacent to said first fold line.

8. A retainer card in accordance with claim 7, wherein each opening of said second set of openings is substantially aligned with a corresponding opening of said first set of openings when said main section and said center section are folded relative to each other about said first fold line.

9. A retainer card in accordance with claim 8, wherein said main section is substantially juxtaposed to said center section when said main section and said center section are folded relative to each other about said first fold line.

10. A retainer card in accordance with claim 9, wherein said main section includes a set of curved slits and a third set of spaced-apart openings formed from said set of curved slits, each opening of said third set of openings cooperating with an aligned pair of said first and second sets of openings to form a corresponding receptacle for a medical device, whereby said retainer card includes a plurality of receptacles for a plurality of medical devices.

11. A retainer card in accordance with claim 10, wherein each curved slit of said set of curved slits forms a tab extending in a third direction substantially opposite said first direction.

12. A retainer card in accordance with claim 11, wherein said at least one tab and said at least another tab underlie a medical device which has been inserted into said at least one receptacle.

13. A packaging assembly for a medical device, comprising an outer envelope; and an inner retainer card contained within said envelope, said retainer card including a foldable panel having a main section, a center section, and an end section, said main section connected to said center section at a first fold line along one side of said center section, said end section connected to said center section at a second fold line along an opposite side of said center section said center section positioned between said first fold line and said second fold line, said main section and said center section being deflectable from a relaxed, planar configuration to a flexed configuration in which said first fold line forms a ridge and in which said center section assumes an angular position relative to said main section to thereby from a trough underlying said ridge, at least one opening formed in said main section, and at least another opening formed in said center section, said at least another opening cooperating with said at least one opening to form at least one receptacle for a medical device when said main section and said center section are folded into said flexed configuration, said main section including at least one tab attached to an edge of said at least one opening and extending into said trough in a first direction, and said end section including at least another tab extending into said trough in a second direction substantially opposite said first direction.

14. A package assembly in accordance with claim 13, wherein said at least one opening includes a first set of spaced-apart openings.

15. A package assembly in accordance with claim 14 wherein said first set of openings is formed in said main section.

16. A package assembly in accordance with claim 15, wherein said first et of openings is positioned substantially adjacent to said first fold line.

17. A package assembly in accordance with claim 16, wherein said at least another opening includes a second set of spaced-apart openings.

18. A package assembly in accordance with claim 17, wherein said second set of openings is formed in said center section.

19. A package assembly in accordance with claim 18, wherein said second set of openings is positioned substantially adjacent to said first fold line.

20. A package assembly in accordance with claim 19, wherein each of said second set of openings is substantially aligned with a corresponding opening of said first set of openings when said main section and said center section are folded relative to each other about said first fold line.

21. A package assembly in accordance with claim 20, wherein said main section is substantially juxtaposed to said center section when said main section and said center section are folded relative to each other about said first fold line.

22. A package assembly in accordance with claim 21, wherein said main section includes a set of curved slits and a third set of spaced-apart openings formed from said set of curved slits, each opening of said third set of openings cooperating with an aligned pair of said first and second sets of openings to form a corresponding receptacle for a medical device, whereby said retainer card includes a plurality of receptacles for a plurality of medical devices.

23. A retainer card in accordance with claim 22, wherein each curved slit of said set of curved slits forms a tab extending in a third direction substantially opposite said first direction.

24. A package assembly in accordance with claim 23, wherein said at least one tab and said at least another tab underlie a medical device which has been inserted into said at least one receptacle.

* * * * *